United States Patent [19] [11] 4,001,315
Strike [45] Jan. 4, 1977

[54] PROSTAGLANDIN DERIVATIVES
[75] Inventor: Donald P. Strike, St. Davids, Pa.
[73] Assignee: American Home Products Corporation, New York, N.Y.
[22] Filed: Oct. 10, 1975
[21] Appl. No.: 621,452

Related U.S. Application Data

[63] Continuation-in-part of Ser. No. 505,802, Sept. 13, 1974, abandoned.
[52] U.S. Cl. .................. 260/514 D; 260/468 D; 424/305; 424/317
[51] Int. Cl.² ................................. C07C 177/00
[58] Field of Search ................ 260/468 D, 514 D

[56] References Cited
UNITED STATES PATENTS
3,959,303  5/1976  Strike .................. 260/514

Primary Examiner—Robert Gerstl
Attorney, Agent, or Firm—Robert Wiser

[57] ABSTRACT

Derivatives of 11-deoxy-$PGE_2$ are prepared. These new compounds not heretofore found in nature possess various pharmacological activities, one of which is the inhibition of gastric secretion.

4 Claims, 1 Drawing Figure

PROSTAGLANDIN DERIVATIVES

CROSS-REFERENCE TO COPENDING APPLICATION

This application is a continuation-in-part of copending application Ser. No. 505,802, filed Sept. 13, 1974, now abandoned.

BACKGROUND OF THE INVENTION

The prostaglandins are a group of hormone-like substances which may be viewed as derivatives of prostanoic acid. Several protaglandins are found widely distributed in mammalian tissue and have been isolated from this source. These prostaglandins have been shown to possess a variety of biological properties such as bronchodilation and the ability to reduce gastric secretion.

The present invention concerns $PGE_2$ derivatives in which the 11-position (using the prostanoic acid numbering system) is a methylene group, i.e. the 11-hydroxyl group normally present in $PGE_2$ has been removed and is replaced with hydrogen. The preparation of the parent molecule of this series, 11-deoxy-$PGE_2$, is reported in J. Org. Chem. 38, 951 (1973).

SUMMARY OF THE INVENTION

The invention sought to be patented in a first composition aspect resides in the concept of a chemical compound of the structure

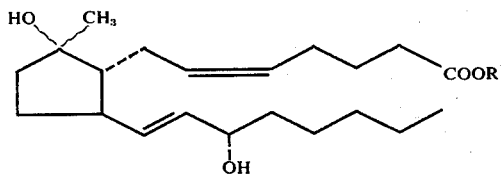

wherein R is hydrogen or alkyl of from 1 to 6 carbon atoms.

The tangible embodiments of the first composition aspect of the invention possess the inherent general physical properties of being clear to yellow oils, are substantially insoluble in water and are generally soluble in organic solvents such as ethyl acetate and ether. Examination of compounds produced according to the hereinafter described process reveals, upon infrared, nuclear magnetic resonance, and mass spectragraphic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the first composition aspect of the invention possess the inherent applied use characteristic of exerting hypotensive effects, and when the 9-methyl group is in the β configuration, gastric anti-secretory effects, upon administration to warm-blooded animals. These effects are evidenced by pharmacological evaluation according to standard test procedures.

The invention sought to be patented in a second composition aspect resides in the concept of a chemical compound of the structure

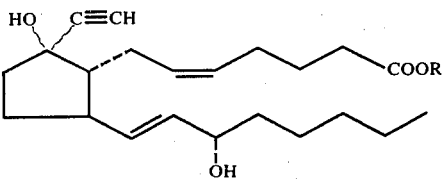

wherein R is H or alkyl of from 1 to 6 carbon atoms.

The tangible embodiments of the second composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the second composition aspect of the invention possess the inherent applied use characteristic of exerting hypotensive effects upon administration to warm-blooded animals as evidenced by pharmacological evaluation according to standard test procedures, and, in addition, are useful as intermediates in the synthesis of the embodiments of the fourth composition aspect of the invention.

The invention sought to be patented in a third composition aspect resides in the concept of a chemical compound of the structure

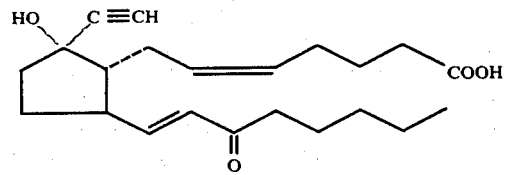

The tangible embodiments of the third composition aspect of the invention possess the inherent general physical properties of being clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the third composition aspect of the invention possess the inherent applied use characteristic of being intermediates in the synthesis of the embodiments of the fourth composition aspect of the invention.

The invention sought to be patented in a fourth composition aspect resides in the concept of a chemical compound of the structure

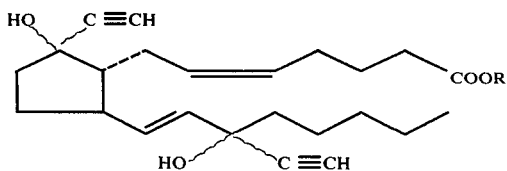

wherein R is hydrogen or alkyl of from 1 to 6 carbon atoms.

The tangible embodiments of the fourth composition aspect of the invention possess the inherent general physical properties of being either crystalline solids or clear to yellow oils, are substantially insoluble in water and are generally soluble in polar solvents such as ethyl acetate and ether. Examination of compounds produced according to the hereinafter described process reveals, upon infrared, nuclear magnetic resonance, and mass spectrographic analysis, spectral data supporting the molecular structures herein set forth. The aforementioned physical characteristics, taken together with the nature of the starting materials, and the mode of synthesis, confirm the structure of the compositions sought to be patented.

The tangible embodiments of the fourth composition aspect of the invention possess the inherent applied use characteristic of exerting bronchodilating and gastric anti-secretory effects upon administration to warm-blooded animals as evidenced by pharmacological evaluation according to standard test procedures. The tangible embodiments of the fourth composition aspect of the invention exhibit anti-hypertensive effects upon administration to warm-blooded animals as evidenced by pharmacological evaluation according to standard test procedures.

DESCRIPTION OF THE PREFERRED EMBODIMENTS

Figure 1:
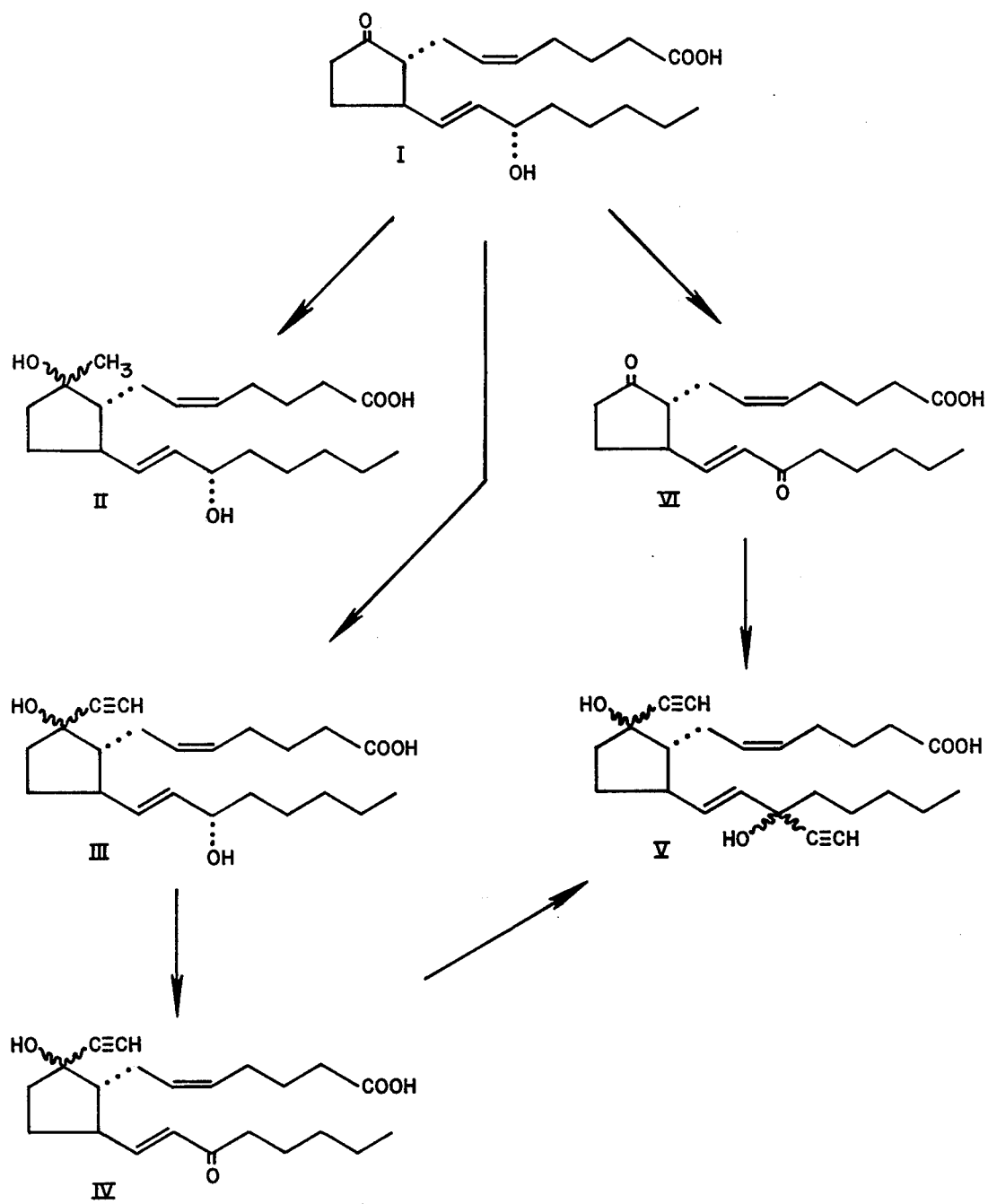

In describing the synthesis of the compositions of the invention, reference will be made to FIG. 1, wherein is illustrated the preparation of specific embodiments of the invention, and wherein the formulae representing the various aspects of the invention are assigned Roman numerals for purposes of identification. Additionally, in order to designate the stereochemistry of various substituents on the prostaglandin skeleton, different types of lines are utilized when representing the bonds of said substituents. Thus, with reference to the plane of the paper, when a dashed line ( - - - - ) is used, the substituent will be understood to be in the $\alpha$ (down) configuration; when a heavy line (━) is used, the substituent will be understood to be in the $\beta$ (up) configuration; and when a wavy line (〰) is used both $\alpha$ and $\beta$ configurations are contemplated for the substituent. Thus, for example, when a new assymetric center is created by a below-described reaction, for example the addition of a Grignard reagent to a ketone, since both possible configurations for the new substituents will be produced they will be denoted by wavy lines (〰). Both of said isomers, unless otherwise noted, are considered to be full equivalents for the purposes of this invention. For purposes of convenience, the formulae in FIG. 1 are all free carboxylic acids; however, it will be obvious to those skilled in the art that these free acids may readily be esterified as for example with diazomethane, or with an alkanol and the proper catalyst. These esters are considered to be full equivalents to the free acids for the purposes of the invention. Finally, the use of specific embodiments in FIG. 1 to illustrate the invention is merely descriptive and is not intended to delimit the scope of the invention.

The starting material for the synthesis of the compounds of the invention is 11-deoxy-PGE$_2$ (I) which may be prepared synthetically as described, for example, in J. Org. Chem. 38, 951 (1973). Referring now to FIG. 1, 11-deoxy-PGE$_2$ (I) may first be reacted with a methyl metallic reagent, such as methyl magnesium bromide, methyl magnesium iodide, or methyl lithium producing the diol II. The isomers of II may be separated by, for example, chromatography.

Alternatively, I may first be reacted with an ethynyl metallic reagent such as ethynyl magnesium bromide or lithium acetylide producing the diol III. The allylic alcohol function of III may next be oxidized producing the ketone IV. This oxidation may be accomplished, for example, by use of Jones reagent. The ketone IV may next be treated with an ethynyl metallic reagent, for example ethynyl magnesium bromide or lithium acetylide producing the diethynyl-diol V. Finally, I may first be oxidized with for example, Jones reagent producing the di-ketone VI. This di-ketone may next be reacted with an ethynyl metallic reagent such as ethynyl magnesium bromide or lithium acetylide producing the di-ethynyl-diol V.

Various compounds of the invention bear carboxyl groups and can be readily converted to their respective alkali metal salts or a salt of a pharmacologically acceptable cation derived from ammonia or a basic amine. All such salts are full equivalents of the subject matter particularly claimed.

In using the compounds of the invention to produce bronchodilating effects in warm-blooded animals, they may be administered in a variety of dosage forms: oral, injectable, and aerosol inhalation. Aerosol inhalation is a preferred method because of its rapid onset of action, great potency, and specificity of action. The particular dosage to obtain the bronchodilating effect will vary with the particular compound employed, the particular animal involved, and the degree of bronchodilation desired. In the guinea pig, by aerosol inhalation, the dose to produce bronchodilation is from about 0.15 micrograms to about 25 micrograms, and preferably from about 0.15 to about 15 micrograms. The bronchodilation produced upon aerosol inhalation can be observed by the method of Rosenthale et al., J. Pharmacol. Exp. Ther., 178, 541 (1971). Using this procedure the following result was obtained.

| Compound | Dose (mg) | Percent Inhibition of the bronchoconstricting effects of a standard dose of acetylcholine |
|---|---|---|
| 7-[(5RS)-5-ethynyl-2$\beta$-([3RS]-3-ethynyl-3-hydroxy-trans-1-octenyl)-5-hydroxy-1$\alpha$-cyclo- | 0.15 | 48 |

| Compound | Dose (mg) | Percent Inhibition of the bronchoconstricting effects of a standard dose of acetylcholine |
|---|---|---|
| pentyl]-cis-5-heptenoic acid | | |

In the use of the compounds of the invention to produce hypotensive effects in warm-blooded animals, administration by the injectable route is preferred, preferably the intravenous route.

Thus in the anesthetized dog by the intravenous route the dose to produce hypotension is from about 1 mg/kg. to about 200 mg/kg. and preferably from about 10 mg/kg. to about 100 mg/kg. Using this procedure the following results were obtained.

| Compound | Dose (mg/kg.) | Δb.p. (mm. Hg) |
|---|---|---|
| 7-(5α-hydroxy-2β-[(3S)-3-hydroxy-trans-1-octenyl]-5β-methyl-1α-cyclopentyl)-cis-5-heptenoic acid | 100 | −23 |
| 7-(5β-hydroxy-2β-[(3S)-3-hydroxy-trans-1-octenyl]-5α-methyl-1α-cyclopentyl)-cis-5-heptenoic acid | 100 | −19 |
| 7-([5RS)-5-ethynyl-5-hydroxy-2β-[(3S)-3-hydroxy-trans-1-octenyl]-1α-cyclopentyl)-cis-5-heptenoic acid | 10 | −40 |
| 7-([5RS]-5-ethynyl-2β-[(3RS)-3-ethynyl-3-hydroxy-trans-1-octenyl]-5-hydroxy-1α-cyclopentyl)-cis-5-heptenoic acid | 100 | −26 |

In the rat by the interduodenal route the dose to inhibit gastric secretion is from about 0.1 mg/kg. to about 25 mg/kg. and preferably from about 0.5 mg/kg. to about 10 mg/kg. The reduction in gastric secretion can be observed by a modification of the method of Shay et al., Gastroenterology, 26, 906 (1954). Using this procedure the following results were obtained.

| Compound | Dose (mg/kg.) | Results |
|---|---|---|
| 7-(5α-hydroxy-2β-[(3S)-3-hydroxy-trans-1-octenyl]-5β-methyl-1α-cyclopentyl)-cis-5-heptenoic acid | 4 | Statistically significant decrease in total gastric volume, and hydrogen ion secreted. |
| 7-([5RS]-5-ethynyl-2β-[(3RS)-3-ethynyl-3-hydroxy-trans-1-octenyl]-5-hydroxy-1α-cyclopentyl)-cis-5-heptenoic acid | 4 | Statistically significant decrease in concentration of hydrogen ion in gastric juice. |

The following examples further illustrate the best mode contemplated by the inventor for the practice of the invention.

EXAMPLE 1

7-(5α-Hydroxy-2β-[(3S)-3-Hydroxy-Trans-1-Octenyl]-5β-Methyl-1α-Cyclopentyl)-Cis-5-Heptenoic Acid (9β-CH$_3$, II) and 7-(5β-Hydroxy-2β-[(3S)-3-Hydroxy-Trans-1-Octenyl]-5α-Methyl-1α-Cyclopentyl)-Cis-5-Heptenoic Acid (9α-CH$_3$, II)

An ice-cooled solution of 0.99 g. of 7-(2β-[(3S)-3-hydroxy-trans-1-octenyl]-5-oxo-1α-cyclopentyl)-cis-5-heptenoic acid in 50 ml. of tetrahydrofuran was treated dropwise with 4.8 ml. of 3M methyl magnesium bromide in ether and the mixture stirred at 0° for ½ hour under nitrogen. The mixture was diluted with ammonium chloride solution, acidified with acetic acid and extracted with ether. After washing and drying, the extract was evaporated and the residue chromatographed on silica with 40% ethyl acetate in hexane to obtain 0.09 g. of 7-(5α-hydroxy-2β-[(3S)-3-hydroxy-trans-1-octenyl]-5β-methyl-1α-cyclopentyl)-cis-5-heptenoic acid, as an oil, $\lambda_{max}^{film}$ 3.0, 3.45, 5.8, 8.1, 10.3 μ. NMR: δ 5.5 (m, 4, olefinic H), 5.18 (s, 3, OH), 4.1 (m, 1, 15-H), 1.32 (s, 9-CH$_3$) ppm. Mass spectrum: M$^+$-H$_2$O at m/e 334.

Continued elution afforded 0.13 g. of 7-(5β-hydroxy-2β-[(3S)-3-hydroxy-trans-1-octenyl]-5α-methyl-1α-cyclopentyl)-cis-5-heptenoic acid as an oil, $\lambda_{max}^{film}$ 3.0, 3.45, 5.8, 8.1, 10.3 μ. NMR: δ 5.5 (m, 7, 4-olefinic and 3-OH), 4.1 (m, 1, 15-H), 1.2 (s, 9-CH$_3$) ppm. Mass spectrum: M$^+$-H$_2$O at 334.

EXAMPLE 2

7-[(5RS)-5-Ethynyl-5-Hydroxy-2β-((3S)-3-Hydroxy-Trans-1-Octenyl)-1α-Cyclopentyl]-Cis-5-Heptenoic Acid III Add a solution of 1.0 g. of 7-[2β-((3S)-3-hydroxy-trans-1-octenyl)-5-oxo-1α-cyclopentyl]-cis-5-heptenoic acid in 30 ml. of tetrahydrofuran dropwise over 5 minutes to a solution of ethynyl magnesium bromide (prepared from 9.7 ml. of 3M methyl magnesium bromide and excess acetylene) in 110 ml. of tetrahydrofuran and stir the mixture at 25° under nitrogen for 1 hour. Add the reaction mixture to aqueous ammonium chloride solution, acidify with acetic acid and extract with ether. After washing and drying, evaporate the ether extract and chromatograph the residue on silica with 30% ethyl acetate in hexane to obtain 0.825 g. of 7-[(5RS)-5-ethynyl-5-hydroxy-2β-((3S)-3-hydroxy-trans-1-octenyl)-1α-cyclopentyl]-cis-5-heptenoic acid as an oil, $\lambda_{max}^{film}$ 3.0, 3.45, 4.7 (weak), 8.5, 8.1, 10.3μ. NMR: δ 5.6 (m, 4, olefinic), 4.2 (m, 1, 15-H), 2.15 and 2.02 (s, C CH) ppm. Mass spectrum: M$^+$-H$_2$O at m/e 344.2353 (theory 344.2350).

EXAMPLE 3

7-[2β-(3-Oxo-Trans-1-Octenyl)-(5RS)-5-Ethynyl-5-Hydroxy-1α-Cyclopentyl]-Cis-5-Heptenoic Acid IV Treat an ice-cooled solution of 7-[(5RS)-5-ethynyl-5-hydroxy-2β-([3S]-3-hydroxy-trans-1-octenyl)-1α- cyclopentyl]-cis-5-heptenoic acid in acetone dropwise with Jones reagent until the orange color persists (approximately 1.5 equivalents). Stir the reaction mixture at 0° for 40 minutes, add methanol to destroy the excess reagent and saturated aqueous sodium bicarbonate until basic. Dilute the mixture with water, acidify with acetic acid and extract with ether. After washing and drying, evaporate the ether extract and chromatograph the residue on silica with ethyl acetate in hexane to obtain 7-[2β-(3-oxo-trans-1-octenyl)-(5RS)-5-ethynyl-5-hydroxy-1α-cyclopentyl]-cis-5-heptenoic acid.

EXAMPLE 4

7-[(5RS)-5-Ethynyl-2β-((3RS)-3-Ethynyl-3-Hydroxy-Trans-1-Octenyl)-5-Hydroxy-1α-Cyclopentyl]-Cis-5-Heptenoic Acid V Add a solution of 7-[2β-(3-oxo-trans-1-octenyl)-(5RS)-5-ethynyl-5-hydroxy-1α-cyclopentyl]-cis-5-heptenoic acid in tetrahydrofuran to a solution of ethynyl magnesium bromide (prepared from 3M methyl magnesium bromide and excess acetylene) in tetrahydrofuran and keep the mixture at 25° for 2 hours. Add the reaction mixture to aqueous ammonium chloride solution, acidify with acetic acid and extract with ether. After washing and drying, evaporate the ether extract and chromatograph the residue on silica with 25% ethyl acetate in hexane to obtain 7-[(5RS)-5-ethynyl-2β-((3RS)-3-ethynyl-3-hydroxy-trans-1-octenyl)-5-hydroxy-1α-cyclopentyl]-cis-5-heptenoic acid as an oil, $\lambda_{max}^{film}$ 3.0, 3.4, 4.7, 5.75, 8.0, 10.25 μ. NMR: δ 5.6 (m, 4, olefinic), 2.6 (m, C CH) ppm. Mass spectrum: M⁺ at m/e 386.

EXAMPLE 5

7-[2β-(3-Oxo-Trans-1-Octenyl)-5-Oxo-1α-Cyclopentyl]-Cis-5-Heptenoic Acid VI

Treat an ice-cooled solution of 7-[2β-((3S)-3-hydroxy-trans-1-octenyl)-5-oxo-1α-cyclopentyl]-cis-5-heptenoic acid in acetone dropwise with Jones reagent until the orange color persists (approximately 1.5 equivalents). Stir the reaction mixture at 0° for 40 minutes, add methanol to destroy the excess reagent and saturated aqueous sodium bicarbonate until basic. Dilute the mixture with water, acidify with acetic acid and extract with ether. After washing and drying, evaporate the ether extract and chromatograph the residue on silica with ethyl acetate in hexane to obtain 7-[2β-(3-oxo-trans-1-octenyl)-5-oxo-1α-cyclopentyl]-cis-5-heptenoic acid as an oil, $\lambda_{max}^{film}$ 3.45, 5.75, 5.85, 6.0, 6.15, 6.85, 7.1, 7.2, 8.7, 10.2 μ. UV: $\lambda_{max}^{EtOH}$ 228 Mμ (ε 11,860). NMR: δ 0.90 (t, 3, methyl); 5.40 (m, 2, 5 and 6-H); 6.18 (J=16, 14-H); 6.86 (dd, J=16 and 7.5, 13-H); 10.72 (s, 1, OH) ppm.

EXAMPLE 6

7-[(5RS)-5-Ethynyl-2β-((3RS)-3-Ethynyl-3-Hydroxy-Trans-1-Octenyl)-5-Hydroxy-1α-Cyclopentyl]-Cis-5-Heptenoic Acid V Add a solution of 0.5 g. of 7-[2β-(3-oxo-trans-1-octenyl)-5-oxo-1α-cyclopentyl]-cis-5-heptenoic acid in 5 ml. of tetrahydrofuran to a solution of ethynyl magnesium bromide (prepared from 5.0 ml. of 3M methyl magnesium bromide and excess acetylene) in 50 ml. of tetrahydrofuran and keep the mixture at 25° for 2 hours. Add the reaction mixture to aqueous ammonium chloride solution, acidify with acetic acid and extract with ether. After washing and drying, evaporate the ether extract and chromatograph the residue on silica with 25% ethyl acetate in hexane to obtain 0.265 g. of 7-[(5RS)-5-ethynyl-2β-((3RS)-3-ethynyl-3-hydroxy-trans-1-octenyl)-5-hydroxy-1α-cyclopentyl]-cis-5-heptenoic acid as an oil, $\lambda_{max}^{film}$ 3.0, 3.4, 4.7, 5.75, 8.0, 10.25 μ. NMR: δ 5.6 (m, 4, olefinic), 2.6 (m, C CH) ppm. Mass spectrum: M⁺ at m/e 386.

The subject matter which the applicant regards as his invention is particularly pointed out and distinctly claimed as follows:

1. A chemical compound of the structure:

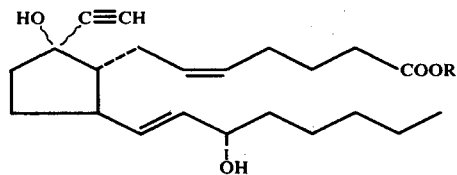

wherein R is hydrogen or alkyl of from 1 to 6 carbon atoms.

2. The chemical compound of claim 1 wherein R is hydrogen.

3. A chemical compound of the structure:

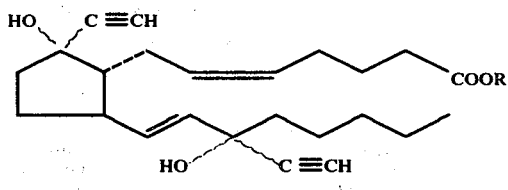

wherein R is hydrogen or alkyl of from 1 to 6 carbon atoms.

4. The chemical compound of claim 3 wherein R is hydrogen.

* * * * *